(12) United States Patent
Richard et al.

(10) Patent No.: US 8,367,096 B2
(45) Date of Patent: Feb. 5, 2013

(54) POLYMERS HAVING COVALENTLY BOUND THERAPEUTIC AGENTS

(75) Inventors: Robert E. Richard, Wrentham, MA (US); Rudolf Faust, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1136 days.

(21) Appl. No.: 11/184,223

(22) Filed: Jul. 19, 2005

(65) Prior Publication Data

US 2007/0020308 A1    Jan. 25, 2007

(51) Int. Cl.
*A61F 2/00* (2006.01)
(52) U.S. Cl. ....................................................... 424/426
(58) Field of Classification Search .................. None
See application file for complete search history.

(56) References Cited

U.S. PATENT DOCUMENTS

| | | | | |
|---|---|---|---|---|
| 5,474,767 A | * | 12/1995 | Tremont | 424/78.27 |
| 5,629,386 A | * | 5/1997 | Osman | 525/354 |
| 5,733,925 A | | 3/1998 | Kunz et al. | 514/449 |
| 5,827,925 A | * | 10/1998 | Tremont et al. | 525/102 |
| 6,051,657 A | | 4/2000 | Faust et al. | 525/284 |
| 6,194,597 B1 | | 2/2001 | Faust et al. | 556/488 |
| 6,268,451 B1 | | 7/2001 | Faust et al. | 526/279 |
| 6,322,815 B1 | | 11/2001 | Saltzman et al. | 424/486 |
| 6,469,115 B1 | | 10/2002 | Faust et al. | 526/194 |
| 6,471,955 B1 | * | 10/2002 | Tremont et al. | 424/78.18 |
| 2002/0122785 A1 | | 9/2002 | Stein et al. | 424/78.27 |
| 2003/0220447 A1 | | 11/2003 | Harris et al. | 525/54.1 |
| 2003/0224033 A1 | * | 12/2003 | Li et al. | 424/423 |
| 2004/0076602 A1 | | 4/2004 | Harris et al. | 424/78.38 |
| 2004/0213759 A1 | | 10/2004 | Zalipsky et al. | 424/78.27 |
| 2005/0220882 A1 | * | 10/2005 | Pritchard et al. | 424/488 |

FOREIGN PATENT DOCUMENTS

| | | |
|---|---|---|
| WO | WO 01/87999 A2 | 11/2001 |
| WO | WO 02/28924 A1 | 4/2002 |
| WO | 2004/100926 A2 | 11/2004 |
| WO | WO 2005/118018 A1 | 12/2005 |
| WO | WO 2006/014606 A2 | 2/2006 |

OTHER PUBLICATIONS

W.E. Perkins, et al., "Polymer Delivery of the Active Isomer of Misoprostol: A Solution to the Intestinal Side Effect Problem", *The Journal of Pharmacology and Experimental Therapeutics*, 1994, vol. 269, No. 1, pp. 151-156.
Christine M. DiBlasi, et al., "An Acid-Stable *tert*-Butyldiarylsilyl (TBDAS) Linker for Solid-Phase Organic Synthesis", *Organic Letters*, 2005, vol. 7, No. 9, pp. 1777-1780.
Joseph P. Kennedy, et al., "Carbocationic Synthesis and Characterization of Polyolefins with Si—H and Si—Cl Head Groups", *Polymerizations and Polymer Properties*, vol. 43, 1982, pp. 1-50.
Laszlo Sipos, et al., "Controlled Delivery of Paclitaxel from Stent Coatings Using Poly(hydroxystyrene-*b*-hydroxystyrene) and its Acetylated Derivative", *Biomacromolecules*, 2005, vol. 6, pp. 2570-2582.
Jae Cheol Cho, et al., Synthesis Characterization, Properties, and Drug Release of Poly(alkyl methacrylate-*b*-isobutylene-*b*-alkyl methacrylate), *Biomacromolecules*, 2006, vol. 7, pp. 2997-3007.
Kunal Sarkar, et al., "Coronary Artery Restenosis: Vascular Biology and Emerging Therapeutic Strategies", *Expert Review of Cardiovascular Therapy, Future Drugs*, vol. 4, No. 4, 2006, pp. 543-556.

* cited by examiner

*Primary Examiner* — Paul Dickinson
(74) *Attorney, Agent, or Firm* — Mayer & Williams PC; David B. Bonham; Keum J. Park

(57) ABSTRACT

Therapeutic polymers are described, which contain at least one polymeric portion and at least one therapeutic agent. The therapeutic agent and the polymeric portion are covalently linked via one or more linkages which hydrolyze in an aqueous environment, for example, one or more linkages selected from an Si—N linkage, an Si—O linkage, and a combination of the same. Other aspects the invention are directed to methods of making the above therapeutic polymers.

20 Claims, No Drawings

POLYMERS HAVING COVALENTLY BOUND THERAPEUTIC AGENTS

FIELD OF THE INVENTION

The present invention relates generally to polymers having bound therapeutic agents, and more particularly to polymers having bound therapeutic agents which are readily released from the polymer under aqueous conditions, and which are useful in a number of settings, including use in medical devices.

BACKGROUND OF THE INVENTION

Numerous polymer-based medical devices have been developed for the delivery of therapeutic agents to the body. For example, many state of the art medical devices consist of a device with a biostable or biodegradable polymeric coating that serves as the reservoir for one or more therapeutic agents. Ways to change the release rate of the therapeutic agent from the coating include changing the therapeutic agent loading, adding additional polymers (e.g., to change the hydrophilic/hydrophobic balance of the coating), the use of polymeric barrier layers, and so forth. Examples include drug eluting coronary stents, which are commercially available from Boston Scientific Corp. (TAXUS), Johnson & Johnson (CYPHER), and others.

Many types of polymeric materials have been used as the reservoir matrix into which the therapeutic agent is placed. Examples include polyisobutylene (PIB) based block copolymers, poly(butyl methacrylate), and poly(vinyl acetate), among others. It has been found that block copolymers based on polyisobutylene are particularly biostable and biocompatible, especially in the coronary artery which has been of particular interest for the development of drug eluting stents.

There is a continuing need for high performance polymeric materials that regulate the release of therapeutic agents, including those for use in medical devices.

SUMMARY OF THE INVENTION

According to an aspect of the present invention, therapeutic polymers are provided, which contain at least one polymeric portion and at least one therapeutic agent. The therapeutic agent and the polymeric portion are covalently linked via one or more linkages which hydrolyze in an aqueous environment, for example, one or more linkages selected from an Si—N linkage, an Si—O linkage, and a combination of the same.

Other aspects of the invention are directed to methods of making the above therapeutic polymers.

According to other aspects of the invention, therapeutic compositions comprising the above therapeutic polymers are provided, which can be administered to a wide variety of subjects, including eukaryotic subjects, such as plants and animals, for a variety of therapeutic purposes.

An advantage of the present invention is that linking moieties are provided which are capable of linking a broad range of therapeutic agents to a broad range of polymers.

Another advantage of the present invention is that polymers are provided with linked therapeutic agents, which are readily released under aqueous conditions.

Yet another advantage of the present invention is that polymers are provided, which can be therapeutically administered to a wide range of plants and animals.

These and other aspects, embodiments and advantages of the present invention will become immediately apparent to those of ordinary skill in the art upon review of the Detailed Description and Claims to follow.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention.

All publications, patents and patent applications cited herein, whether supra or infra, are hereby incorporated by reference in their entirety.

As noted above, in one aspect, the present invention provides therapeutic polymers which contain at least one polymeric portion and at least one covalently attached therapeutic agent. The therapeutic agent and the polymeric portion are covalently linked via one or more linkages which hydrolyze in an aqueous environment (e.g., via one or more Si—N linkages, one or more Si—O linkages, or a combination of Si—N and Si—O linkages), thereby releasing the therapeutic agent.

As used herein, "polymers" and "polymeric portions" are molecules and portions of molecules, respectively, that contain multiple copies of one or more constitutional units, commonly referred to as monomers, typically from 2 to 5 to 10 to 25 to 50 to 100 or even more constitutional units. An example of a common linear polymer is polystyrene

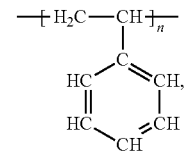

where n is an integer, in which the polymer contains styrene monomers

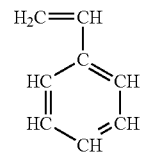

(i.e., the polymer originates from, or has the appearance of originating from, the polymerization of styrene monomers, in this case, the addition polymerization of styrene monomers).

Therapeutic polymers for use in the present invention can have a variety of architectures, including cyclic, linear and branched architectures. Branched architectures include star-shaped architectures (e.g., architectures in which three or more chains emanate from a single branch point), comb architectures (e.g., architectures having a main chain and a plurality of side chains) and dendritic architectures (e.g., arborescent and hyperbranched polymers), among others.

The therapeutic polymers for use the present invention can contain, for example, homopolymers, which contain multiple copies of a single constitutional unit, and copolymers, which contain multiple copies of at least two dissimilar constitutional units, which units may be present in any of a variety of distributions including random, statistical, gradient, and periodic (e.g., alternating) distributions.

As used herein, "low glass transition temperature ($T_g$) monomers" are those that, when self-polymerized, form homopolymers displaying a $T_g$ that is below ambient temperature, more typically below about 20° C., below about 0° C., below about −25° C., or even below about −50° C. "Ambient temperature" is 25° C.-45° C., more typically body temperature (e.g., 35° C.-40° C.). Conversely, elevated or "high $T_g$ monomers" are those that, when self-polymerized, form homopolymers displaying a glass transition temperature that is above ambient temperature, more typically above 50° C., above 75° C. or even above 100° C. $T_g$ can be measured by any of a number of techniques including differential scanning calorimetry (DSC), dynamic mechanical analysis (DMA), or dielectric analysis (DEA). Polymers formed from low $T_g$ monomers are typically soft and elastomeric at ambient temperature, whereas polymers formed from high $T_g$ monomers are hard at ambient temperature. A particular example of a low $T_g$ monomer is isobutylene, which has been reported to have a $T_g$ of approximately −73° C. in homopolymer form. A particular example of a high $T_g$ monomer is styrene, which has been reported to have a $T_g$ of approximately 100° C. in homopolymer form.

In embodiments where the therapeutic polymers of the present invention contain both low and high $T_g$ monomers, they may contain, for example, from 50 to 80 wt % low $T_g$ monomer and from 20 to 50 wt % high $T_g$ monomer, among other ranges.

"Block copolymers" are polymers containing two or more differing homopolymer or copolymer chains. In certain embodiments, for example, the therapeutic polymers of the present invention contain (a) one or more polymer chains (designated "L" below) that contain one or more low $T_g$ monomers and (b) one or more additional polymer chains (designated "H" below) that contain one or more high $T_g$ monomers.

Block copolymer configurations vary widely and include, for example, the following configurations (in which H and L chains, are presented, although other chains having different characteristics could clearly be substituted): (a) block copolymers having alternating blocks of the type (HL)$_m$, L(HL)$_m$ and H(LH)$_m$ where m is a positive whole number of 1 or more, (b) block copolymers having multi-arm geometries such as X(LH)$_n$, and X(HL)$_n$, where n is a positive whole number of 2 or more, and X is a hub species (e.g., an initiator molecule residue, a residue of a molecule to which preformed polymer chains are attached, etc.), and (c) comb copolymers having an L chain backbone and multiple H side chains as well as comb copolymers having an H chain backbone and multiple L side chains.

In addition to monomers, therapeutic homopolymers and copolymers in accordance with the present invention may contain a variety of other species. Examples include hub species (such as initiator residues, see above), capping molecules, end groups, linking residues, therapeutics (e.g., those linked by hydrolysable or non-hydrolysable linkages) and so forth.

Therapeutic polymers in accordance with the present invention can be formed in a number of ways, including providing a polymer that contains one or more (e.g., 2, 3, 4, 5 10, 25, 50, 100, etc., or more) chlorosilyl (Si—Cl) groups, and reacting a therapeutic agent that contains one or more groups selected from hydroxyl groups (e.g., C——H), primary and secondary amine groups (e.g., C—NH$_2$ or C—NH—C, assuming neutral charge), and combinations of the same under conditions that lead to the formation of covalent Si—O and Si—N linkages, respectively, between the polymer and therapeutic agent. In general, these reaction conditions include combining the chlorosilane containing polymer and the therapeutic in an anhydrous solvent system along with an HCl scavenger (e.g., pyridine or triethylamine), followed by isolation and purification under anhydrous conditions.

One method of forming polymers that contain chlorosilyl groups is to react polymers having (or which are modified to have) unsaturated (e.g., vinyl) groups with species such as dimethylchlorosilane, (CH$_3$)$_2$SiClH, under catalytic conditions. Suitable polymers for this purpose can be selected, for example, from the list of polymers provided below, from which supplemental polymers for use in the present invention may be selected.

Another method is to form a homopolymer or copolymer from monomers that contain one or more silylchloride groups. In the case of copolymers, for example, one or more monomers, each containing one or more silylchloride groups, and one or more additional monomers, each having or devoid of silylchloride groups, are polymerized simultaneously (leading, for example, to periodic, random, statistical or gradient copolymers) or sequentially (leading, for example, to block copolymers).

The chlorosilyl functionality is somewhat unusual in that it does not need to be protected under cationic polymerization conditions, because it does not react with carbocations or Lewis acids (see, e.g., U.S. Pat. No. 6,051,657 to Faust et al.). Accordingly, monomers for use in forming silyl-chloride-group-containing polymers include cationically polymerizable chlorosilyl-group-containing monomers.

Examples of such monomers include

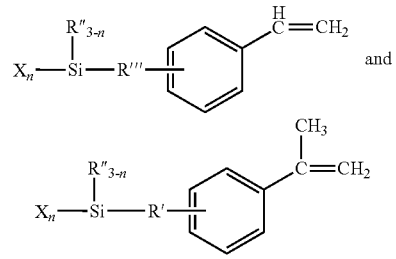

where the R″ groups are independently selected from alkyl groups having 1 to 10 carbon atoms, aryl groups having 6 to 10 carbon atoms, and alkyl-aryl groups having from 7 to 12 carbon atoms, where R′ and R‴ are divalent non-aromatic hydrocarbon groups having 0 to 6 carbon atoms, where the X groups are halogen atoms, and where n is 1, 2 or 3. Such monomers may be prepared, for example, by a hydrosilation reaction between a vinylalkenyl benzene and the corresponding halosilane in the presence of a platinum catalyst, followed by separation by distillation. Two specific examples of such monomers are (2-dichloromethylsilyl-ethyl)styrene (DSiSt) and 1-isopropenyl-3-(1-dichloromethylsilylmethyl)ethylbenzene (IDEB). They are described, for example, in U.S. Pat. Nos. 6,469,115 and 6,268,451 to Faust et al. Also, 4-(chlorodimethylsilyl) styrene is sometimes used in living polymerization of dendritic polymers.

Because they are cationically polymerizable, the above and other silyl-chloride-group-containing monomers can be polymerized along with other cationically polymerizable monomers (e.g., simultaneously or sequentially). Suitable candidates can be selected from one or more of the following known cationically polymerizable monomers: (a) aliphatic olefinic monomers such as propylene, 1-butene, isobutylene, 2-methyl-1-butene, 3-methyl-1-butene, pentene, hexene, cyclohexene, 4-methyl-1-pentene, vinylcyclohexene, octene, and norbornene, among others, (b) vinyl aromatic monomers such as styrene, o-, m-, or p-methylstyrene, □-methylstyrene, □-methylstyrene, 2,6-dimethylstyrene, 2,4-dimethylstyrene, □-methyl-o-methylstyrene, □-methyl-m-methylstyrene, □-methyl-p-methylstyrene, □-methyl-o-methylstyrene, □-methyl-m-methylstyrene, □-methyl-p-methylstyrene, 2,4,6-trimethylstyrene, □-methyl-2,6-dimethylstyrene, □-methyl-2,4-dimethylstyrene, □-methyl-2,6-dimethylstyrene, □-methyl-2,4-dimethylstyrene, o-, m-, or p-chlorostyrene, 2,6-dichlorostyrene, 2,4-dichlorostyrene, □-chloro-o-chlorostyrene, □-chloro-m-chlorostyrene, □-chloro-p-chlorostyrene, □-chloro-o-chlorostyrene, □-chloro-m-chlorostyrene, □-chloro-p-chlorostyrene, 2,4,6-trichlorostyrene, □-chloro-2,6-dichlorostyrene, □-chloro-2,4-dichlorostyrene, □-chloro-2,6-dichlorostyerne, □-chloro-2,4-dichlorostyrene, o-, m-, or p-tert-butylstyrene, o-, m-, or p-methoxystyrene, o-, m-, or p-chloromethylstyrene, o-, m-, or p-bromomethylstyrene, vinylnaphthalene, and indene, among others, (c) diene monomers such as butadiene, isoprene, cyclopentadiene, cyclohexadiene, dicyclopentadiene, divinylbenzene, and ethylidenenorbornene, among others, (d) vinyl ether monomers such as methyl vinyl ether, ethyl vinyl ether, n-propyl vinyl ether, iso-propyl vinyl ether, n-, sec-, tert-, or iso-butyl vinyl ether, methyl propenyl ether, and ethyl propenyl ether, among others, (e) silane compounds such as vinyltrichlorosilane, vinylmethyldichlorosilane, vinyldimethylchlorosilane, vinyldimethylmethoxysilane, vinyltrimethylsilane, divinyldichlorosilane, divinyldimethoxysilane, divinyldimethylsilane, 1,3-divinyl-1,1,3,3-tetramethyldisiloxane, trivinylmethylsilane, □-methacryloyloxypropyltrimethoxysilane, and □-methacryloyloxypropylmethyldimethoxysilane, among others, (f) vinylcarbazole, (g) □-pinene, and (h) acenaphthylene.

In typical cationic polymerization reactions, polymers and copolymers are formed at low temperatures from reaction mixtures that comprise: (a) a solvent system appropriate for cationic polymerization, (b) one or more cationically polymerizable monomer species, (c) an initiator, and (d) a Lewis acid coinitiator. In addition, a proton-scavenger is also typically provided to ensure the practical absence of protic impurities, such as water. Polymerization can be conducted, for example, within a temperature range of from about 0° C. to about –100° C., more typically from about –50° C. to –90° C. Polymerization times are typically those times that are sufficient to reach 50%, 75%, 90%, 95%, 99% or even higher conversions of the monomer species to polymer. Among the solvent systems appropriate for cationic polymerization, many of which are well known in the art, are included: (a) C1 to C4 halogenated hydrocarbons, such as methyl chloride and methylene dichloride, (b) C5 to C8 aliphatic hydrocarbons, such as pentane, hexane, and heptane, (c) C5 to C10 cyclic hydrocarbons, such as cyclohexane and methyl cyclohexane, and (d) mixtures thereof. For example, in some beneficial embodiments, the solvent system contains a mixture of a polar solvent, such as methyl chloride, methylene chloride and the like, and a nonpolar solvent, such as hexane, cyclohexane or methylcyclohexane and the like. Initiators for living carbocationic polymerization are commonly organic ethers, organic esters, organic alcohols, or organic halides, including tert-ester, tert-ether, tert-hydroxyl and tert-halogen containing compounds. Specific examples include alkyl cumyl ethers, cumyl halides, alkyl cumyl esters, cumyl hydroxyl compounds and hindered versions of the same, for instance, dicumyl chloride and 5-tert-butyl, 1,3-dicumyl chloride. Multi-arm polymers, including star polymers can be formed by selecting initiators having three or more initiation sites, for example, tricumyl chloride (i.e., 1,3,5-tris(1-chloroy-1-methylethyl)benzene), which contains three initiation sites. Examples of Lewis acid coinitiators include metal halides such as boron trichloride, titanium tetrachloride and alkyl aluminum halides. The Lewis acid coinitiator is typically used in concentrations equal to or greater, e.g., 2 to 50 times greater, than the concentration of the initiator. Examples of proton-scavengers (also referred to as proton traps) include substituted or unsubstituted 2,6-di-tert-butylpyridines, such as 2,6-di-tert-butylpyridine and 4-methyl-2,6-di-tert-butylpyridine, as well as 1,8-bis(dimethylamino)-naphthalene and diisopropylethyl amine. The concentration of the proton trap is preferably only slightly higher than the concentration of protic impurities such as water in the polymerization system.

Techniques appropriate for forming silylchloride-group-containing copolymers suitable for the practice of the invention can be found, for example, in U.S. Pat. Nos. 6,469,115 and 6,268,115, both to Faust et al.

In accordance with certain embodiments of the invention, one or more cationically polymerizable monomers, each containing one or more silylchloride groups, one or more additional cationically polymerizable monomers, each devoid of a silylchloride group, are reacted.

Specific examples of cationically polymerizable monomers containing one or more silylchloride groups include silylchloride-group-containing styrene monomers such as those described above. Silylchloride-group-containing styrenic blocks may be form by polymerizing such polymers alone or in combination with another styrene monomer which is devoid of silylchloride substitution, such as those described above.

Additional examples of cationically polymerizable monomers that are devoid of silylchloride groups can be found among the aliphatic olefins, vinyl aromatic compounds, dienes, vinyl ethers, silanes, vinylcarbazole, β-pinene, and acenaphthylene described above.

As above, such monomers may be reacted simultaneously, leading, for example, to periodic, random, statistical or gradient copolymers. In such cases, the density of the silylchloride groups within the resulting polymer (and ultimately the density of the covalently attached therapeutic agents), can be varied by varying the ratio of monomers that contain silylchloride groups relative to those that do not. As specific examples, styryl chloride containing polymers can be formed by simultaneously reacting (a) isobutylene with DSiSt and/or IDEB, (b) styrene with DSiSt and/or IDEB or (c) isobutylene with styrene and with DSiSt and/or IDEB. (For specific examples, see U.S. Pat. No. 6,268,451, where isobutylene, IDEB and DSiSt are simultaneously reacted for form a statistical copolymer of the three monomers, and U.S. Pat. No. 6,469,115, where isobutylene and DSiSt are simultaneously reacted to form a random copolymer of the two monomers.)

Such polymers may also be reacted sequentially, leading, for example, to block copolymers. As a specific example, see U.S. Pat. No. 6,469,115, where isobutylene and DSiSt are sequentially reacted for form a block copolymer. With respect to block copolymers having silylchloride containing blocks and non silylchloride containing blocks, the number of silylchloride groups within the polymer (and ultimately the number covalently attached therapeutic agents), can be varied by varying the length of the silylchloride containing blocks and/or the density of the silylchloride groups within such blocks (e.g., where the block also contains monomers devoid of silylchloride groups).

In addition to the above techniques, in which polymers containing chlorosilyl groups are reacted with therapeutic agents that contain hydroxyl and/or amine groups, therapeutic polymers in accordance with the present invention may also be formed by polymerizing a monomer that contains one or more therapeutic agents, covalently linked via one or more linkages selected from an Si—O linkage, an Si—N linkage and a combination of the same.

In some embodiments, copolymers are formed, for example, (a) by polymerizing two different monomers that are covalently linked to therapeutic agents or (b) by polymerizing one or more monomers, each containing one or more covalently linked therapeutic agents, with one or more additional monomers, each devoid of a covalently linked therapeutic agent. Such monomers may be reacted simultaneously (leading, for example, to periodic, random, statistical or gradient copolymers) or sequentially (leading, for example, to block copolymers).

Various synthesis techniques can be employed for this purpose, including the cationic polymerization techniques described above. Depending on the therapeutic agent, various groups my require protection prior to polymerization.

Specific examples of cationically polymerizable monomers with covalently linked therapeutic agents include those formed by reacting silylchloride group containing monomers, such as the styrene monomers described above, with a therapeutic agent that contains hydroxyl, primary amine and/or secondary amine groups. Conditions are described above for reacting such entities so as to form one or more linkages selected from Si—N—C, linkages, Si—O—C linkages, and combinations thereof.

Specific examples of cationically polymerizable monomers that are devoid of covalently linked therapeutic agents can be found among the aliphatic olefins, vinyl aromatic compounds, dienes, vinyl ethers, silanes, vinylcarbazole, β-pinene, and acenaphthylene described above.

Where addition polymerization techniques are employed (e.g., cationic polymerization reactions, such as those described above, are addition polymerization reactions), polymer chains are commonly created which contain a saturated (e.g., in the case of olefin or vinyl polymerization) or unsaturated (e.g., in the case of diolefin polymerization) carbon backbone. Depending on the monomer(s) employed, the carbon backbones can have a wide range of pendant groups. Specific examples include pendant alkyl groups (e.g., where various aliphatic olefins and dienes are employed), pendant substituted and unsubstituted aromatic groups (e.g., where various vinyl aromatic monomers are employed), pendant ethers (e.g., where various vinyl ethers are employed), pendant silane group (e.g., where various silane monomers are employed), and so forth.

Regardless of the technique employed, it should be apparent from the above description that a wide variety of therapeutic polymers in accordance with the present invention can be formed.

Therapeutic polymers in accordance with the present invention can be administered to a wide variety of subjects, including eukaryotic subjects, such as plants and vertebrate subjects, for a variety of therapeutic purposes. By "vertebrate subject" is meant any member of the subphylum cordata, including mammals such as humans and domestic mammals such as cattle, sheep, pigs, goats, horses, camels, buffalo, dogs, cats, and birds, including domestic, wild and game birds such as chickens, turkeys and other gallinaceous birds.

By "therapeutic purpose" is meant an improvement in the size or health of the subject, including the treatment of one or more diseases, pests or conditions. As used herein, "treatment" refers to the prevention of the disease or condition, the reduction or elimination of symptoms associated with the disease or condition, or the substantial or complete elimination of the disease or condition.

In many instances, the therapeutic polymers of the invention are administered in conjunction with a therapeutic article such as a therapeutic composition or a medical device. Modes of administration for the various therapeutic articles of the invention include topical and internal administration. Modes of internal administration to vertebrate subjects include oral, nasal, rectal, vaginal, intracisternal, intradermal, intravaginal, intraperitoneal, topical, bucal, parenteral, and so forth. The term "parenteral" as used herein refers to modes of administration other than through the digestive tract, including intravenous, intraarterial, intramuscular, subcutaneous, peritoneal, and sternal delivery, among other routes.

Examples of therapeutic compositions include various pharmaceutical and agricultural compositions. Therapeutic compositions in accordance with the present invention will frequently include a carrier, for example, a non-toxic solid, semisolid or liquid filler, diluent, encapsulating material or other formulation auxiliary of any type.

Pharmaceutical compositions in accordance with the present invention include powders, granules, solutions, dispersions, emulsions, sprays, aerosols, ointments, gels, creams, drops, tablets, pills, capsules, transdermal patches, suppositories, and so forth. The pharmaceutical compositions may include various pharmaceutically acceptable carriers and/or excipients (e.g., one approved for use in animals/humans). The precise formulation of such compositions will be determined based on the specific therapeutic agents used and the optimal mode of administration. By way of example only, a pharmaceutical carrier may include sterile liquids, such as water and oils. Saline solutions and aqueous dextrose and glycerol solutions may be employed as liquid carriers, particularly for injectable solutions. The therapeutic polymer composition of the invention may be supplied in desiccated form in an ampoule for reconstitution immediately prior to injection. Suitable pharmaceutical excipients may include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, surfactants, pH buffering agents, sustained-release agents, and so forth.

The therapeutic polymers of the invention are also suitable for plant applications, such as use in the release of pesticides, fungicides, herbicides, plant growth-regulatory agents, fertilizers, etc. These agricultural compositions are typically applied topically, or absorbed through the roots, and may include granular agents of relatively large particle size, water-soluble or water-dispersible granules, powdery dusts, wettable powders, pastes, aerosols, aqueous emulsions, solutions, natural or synthetic materials impregnated with therapeutic polymer, microencapsulation of therapeutic polymer in other polymeric materials, or any other agriculturally useful formulation known to those skilled in the art. Suitable surfactants, pH buffering agents, sustained-release agents, etc. may also be included based on specific therapeutic needs and mode of application.

Examples of medical devices include implantable or insertable medical devices, for example, catheters (e.g., renal or vascular catheters such as balloon catheters), guide wires, balloons, filters (e.g., vena cava filters), stents (including coronary vascular stents, peripheral vascular stents, cerebral, urethral, ureteral, biliary, tracheal, gastrointestinal and esophageal stents), stent grafts, vascular grafts, vascular access ports, embolization devices including cerebral aneurysm filler coils (including Guglilmi detachable coils and metal coils), myocardial plugs, patches, pacemakers and pacemaker leads, left ventricular assist hearts and pumps, total artificial hearts, heart valves, vascular valves, biopsy devices, and any coated substrate (which can comprise, for example, glass, metal, polymer, ceramic and combinations thereof) that is implanted or inserted into the body and from which therapeutic agent is released. Examples of medical devices further include patches for delivery of therapeutic agent to intact skin and broken skin (including wounds); sutures, suture anchors, anastomosis clips and rings, tissue staples and ligating clips at surgical sites; cannulae, metal wire ligatures, orthopedic prosthesis such as bone grafts, bone plates, joint prostheses, orthopedic fixation devices such as interference screws in the ankle, knee, and hand areas, tacks for ligament attachment and meniscal repair, rods and pins for fracture fixation, screws and plates for craniomaxillofacial repair; dental devices such as void fillers following tooth extraction and guided-tissue-regeneration membrane films following periodontal surgery; tissue bulking devices, and tissue engineering scaffolds for cartilage, bone, skin and other in vivo tissue regeneration.

The medical devices of the present invention include those used for systemic treatment, as well as the localized treatment of any tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, lungs, trachea, esophagus, intestines, stomach, brain, liver and pancreas, skeletal muscle, smooth muscle, breast, dermal tissue, cartilage, tooth and bone.

In various embodiments, the medical devices are adapted for implantation or insertion into a range of body lumens, including the following: lumens of the cardiovascular system such as the heart, arteries (e.g., coronary, femoral, aorta, ilial, carotid and vertebro-basilar arteries) and veins, lumens of the genitourinary system such as the urethra (including prostatic urethra), bladder, ureters, vagina, uterus, spermatic and fallopian tubes, the nasolacrimal duct, the eustachian tube, lumens of the respiratory tract, such as the trachea, bronchi, nasal passages and sinuses, lumens of the gastrointestinal tract such as the esophagus, gut, duodenum, small intestine, large intestine, colon, biliary and pancreatic duct systems, lumens of the lymphatic system, the major body cavities (peritoneal, pleural, pericardial) and so forth.

Specific examples of implantable or insertable medical devices for use in conjunction with the present invention include vascular stents, such as coronary stents and cerebral stents, which deliver a therapeutic agent into the vasculature for the treatment of restenosis.

In various embodiments, the therapeutic articles of the present invention contain or consist of polymeric release regions, which contain therapeutic polymers in accordance with the present invention, along with other optional supplemental ingredients and supplemental polymers, several of which are set forth below). Polymeric release regions are polymer containing regions, which commonly contain at least 50 wt % polymers (including release polymers), at least 75 wt % polymers, or even more.

In some embodiments, the polymeric release regions of the present invention correspond to an entire therapeutic article. In other embodiments, the polymeric release regions correspond to one or more portions of a therapeutic article. For instance, the polymeric release regions can be in the form of one or more fibers which are incorporated into a medical device, in the form of one or more polymeric layers formed over all or only a portion of an underlying medical device substrate, and so forth. Layers can be provided over an underlying substrate at a variety of locations, and in a variety of shapes (e.g., in desired patterns, for instance, using appropriate masking techniques, such as lithographic techniques), and they can be formed from a variety of polymeric materials. Materials for use as underlying medical device substrates include ceramic, metallic and polymeric substrates. The substrate material can also be a carbon- or silicon-based material, among others. As used herein a "layer" of a given material is a region of that material whose thickness is small compared to both its length and width. As used herein a layer need not be planar, for example, taking on the contours of an underlying substrate. Layers can be discontinuous (e.g., patterned). Terms such as "film," "layer" and "coating" may be used interchangeably herein.

In addition to the attributes of the materials making up the polymeric release regions (e.g., the therapeutic polymers provided therein, as well as any supplemental materials such as supplemental polymers, etc.), the therapeutic agent release profile is also affected by other factors such as the size, number and/or position of the polymeric release regions within the device. For example, the release profile of polymeric release regions in accordance with the present invention can be modified by varying the thickness or surface areas of the same. Moreover, multiple polymeric release regions can be employed to modify the release profile. For example, release layers of the invention, either having the same or different content (e.g., different polymeric and/or therapeutic agent content), can be stacked on top of one another, can be positioned laterally with respect to one another, and so forth.

As a specific example, for tubular devices such as stents (which can comprise, for example, a laser or mechanically cut tube, one or more braided, woven, or knitted filaments, etc.), polymeric release layers can be provided on the luminal surfaces, on the abluminal surfaces, on the lateral surfaces between the luminal and abluminal surfaces (including the ends), patterned along the luminal or abluminal length of the devices, and so forth. Moreover, polymeric release layers can control the release of the same or differing underlying therapeutic agent. It is therefore possible, for example, to release the same or different therapeutic agents at different rates from different locations on the medical device. As another specific example, it is possible to provide a tubular medical device (e.g., a vascular stent) having a first polymeric release layer which contains a first therapeutic agent (e.g., an antithrombotic agent) at its inner, luminal surface and a second polymeric release layer which contains a second therapeutic agent that differs from the first therapeutic agent (e.g., an antiproliferative agent) at its outer, abluminal surface (as well as on the ends, if desired).

As noted above, polymeric release regions of the present invention may also optionally contain materials other that therapeutic polymers, including supplemental polymers, which can be, for example, blended with the above therapeutic polymers.

Examples of supplemental polymers include a variety of homopolymers and copolymers (including alternating, random, statistical, gradient and block copolymers), which may be cyclic, linear or branched (e.g., the polymers may have star, comb or dendritic architecture), which may be natural or synthetic, and which may be thermoplastic or thermosetting. Specific polymers may be selected, for example, from the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides and polyether block amides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, vinyl-aromatic-olefin copolymers, including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene block copolymers such as those disclosed in U.S. Pat. No. 6,545,097 to Pinchuk), polyvinyl ketones, polyvinylcarbazoles, and polyvinyl esters such as polyvinyl acetates; polybenzimidazoles; ethylene-methacrylic acid copolymers and ethylene-acrylic acid copolymers, where some of the acid groups can be neutralized with either zinc or sodium ions (commonly known as ionomers); polyalkyl oxide polymers and copolymers including polyethylene oxides (PEO); polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly(caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and further copolymers of the above.

Supplemental polymers can be provided for various reasons. For instance, supplemental polymers may be introduced (a) to render the polymeric release region more hydrophilic (or more hydrophobic) or less tacky, (b) to modulate the release profile of the therapeutic agent, or (c) to affect one or more of the mechanical characteristics, biostability, biocompatibility, processability, and so forth, of the region.

Numerous techniques are available for forming polymeric regions in accordance with the present invention.

For example, where the therapeutic polymers of the present invention and/or any other supplemental materials to be processed have thermoplastic characteristics, and so long as the therapeutic polymers and any other supplemental materials are sufficiently stable (e.g., so as to avoid substantial reaction/degradation during processing, including hydrolysis of the above described Si—N and Si—O linkages), a variety of standard thermoplastic processing techniques may be used to form the polymeric release regions, including compression molding, injection molding, blow molding, spinning, vacuum forming and calendaring, as well as extrusion into sheets, fibers, rods, tubes and other cross-sectional profiles of various lengths. Using these and other thermoplastic processing techniques, entire devices or portions thereof can be made.

In other embodiments, solvent-based techniques are used to form polymeric release regions in accordance with the present invention. Using these techniques, polymeric release regions can be formed by first providing solutions that contain the therapeutic polymers of the present invention (and/or any other supplemental materials to be processed), and subsequently removing the solvents to form the polymeric release regions. The solvents that are ultimately selected will contain one or more solvent species, which are generally selected based on their ability to dissolve the materials that form the polymeric release region, as well as other factors, including drying rate, surface tension, etc. Moreover, as above, the solutions and processing conditions that are employed are generally selected to ensure the stability of the therapeutic polymers and any other supplemental materials that are present. Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

In some embodiments of the invention, a solution (where solvent-based processing is employed) or a melt (where thermoplastic processing is employed) is applied to a substrate to form a polymeric release region. For example, the substrate can correspond to all or a portion of an implantable or insertable medical device to which a polymeric release region is applied. The substrate can also be, for example, a template, such as a mold, from which the polymeric release region is removed after solidification. In other embodiments, for example, extrusion and co-extrusion techniques, one or more polymeric release regions are formed without the aid of a substrate.

In more specific examples, an entire stent body is extruded or a polymeric release layer is co-extruded along with an underlying stent body. In another specific example, a polymeric release layer is provided on an underlying step body by spraying or extruding a coating layer onto a pre-existing stent body. In yet another more specific example, a stent is cast in a mold.

As used herein "therapeutic agents" are compounds which can result in an improvement in the growth or health of the subject, when administered to the same at an effective dosage level. Therapeutic agents include genetic therapeutic agents, non-genetic therapeutic agents and cells.

As noted above, in the therapeutic polymers of the present invention, therapeutic agents are linked via covalent Si—O and/or Si—N linkages. Suitable therapeutic agents for this purpose include those containing hydroxyl groups, primary amine groups, and secondary amine groups. In addition to covalently linked therapeutic agents, the medical articles of the present invention may also include one or more optional non-covalently bound therapeutic agents.

Several specific examples of therapeutic agents, which may be covalently coupled (where appropriate linking groups such as hydroxyl and amine groups are present, either inherently or by modification of the therapeutic agent) or non-coupled, can be selected, for example, from the therapeutic agents set forth below, among many others.

Non-genetic therapeutic agents for use in conjunction with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) beta-blockers, (u) bARKct inhibitors, (v) phospholamban inhibitors, and (w) Serca 2 gene/protein.

Particularly beneficial non-genetic therapeutic agents include arginine, 2-nitroethanol, paclitaxel (including particulate forms thereof such as ABRAXANE albumin-bound paclitaxel nanoparticles), sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, and Serca 2 gene/protein among others.

Genetic therapeutic agents for use in conjunction with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., PCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in conjunction with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules and precursors including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (O) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

A wide range of therapeutic agent loadings can be used in conjunction with the therapeutic articles of the present invention, with the therapeutically effective amount being readily determined by those of ordinary skill in the art Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A therapeutic article comprising a therapeutic polymer comprising a polymeric portion and a covalently attached therapeutic agent which is linked to the polymeric portion via one or more linkages that hydrolyze in an aqueous environment, wherein said one or more linkages comprise an Si—N linkage, an Si—O linkage, or a combination of the same, wherein said polymeric portion comprises a saturated or unsaturated carbon backbone, alkyl groups directly pendant from said carbon backbone, and pendant aromatic groups, wherein said therapeutic agent is linked to said pendant aromatic groups and wherein said therapeutic article is a medical device that is adapted for implantation or insertion into a lumen of the cardiovascular system.

2. The therapeutic article of claim 1, wherein said medical device is a coronary vascular or peripheral vascular stent.

3. The therapeutic article of claim 1 wherein said medical device comprises a polymeric release region that comprises said therapeutic polymer and a supplemental polymer.

4. The therapeutic article of claim 3 wherein said polymeric release region constitutes the entirety of said medical device.

5. The therapeutic article of claim 3 wherein said polymeric release region constitutes a portion of said medical device.

6. The therapeutic article of claim 3 wherein said polymeric release region is disposed over a medical device substrate.

7. The therapeutic article of claim 3 wherein said polymeric release region is a medical device coating.

8. The therapeutic article of claim 1 wherein said medical device is selected from a guide wire, a balloon, a vena cava filter, a catheter, a stent, a stent graft, a vascular graft, a cerebral aneurysm filler coil, a myocardial plug, a heart valve, a vascular valve, a patch and a tissue engineering scaffold.

9. The therapeutic article of claim 1 wherein said therapeutic agent is covalently attached by reacting a therapeutic agent comprising a functional group selected from hydroxyl groups, amine groups, and combinations of the same with a polymer that comprises a plurality of chlorosilyl groups.

10. The therapeutic article of claim 9 wherein said covalently attached therapeutic agent is derived from an agent selected from anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

11. The therapeutic article of claim 1, wherein said alkyl groups are selected from methyl groups, ethyl groups and combinations of the same.

12. The therapeutic article of claim 1, wherein said polymeric portion comprises a random or alternating copolymer chain.

13. A therapeutic article comprising a therapeutic polymer comprising a polymeric portion and a covalently attached therapeutic agent which is linked to the polymeric portion via one or more linkages that hydrolyze in an aqueous environment, wherein said polymeric portion comprises a saturated or unsaturated carbon backbone and alkyl groups directly pendant from said carbon backbone, wherein said one or more linkages comprise an Si—N linkage, an Si—O linkage, or a combination of the same, wherein said therapeutic article is a medical device that is adapted for implantation or insertion into a lumen of the cardiovascular system, wherein the polymer portion is formed from monomers comprising
  (a) a first halosilyl-group-containing monomer polymerizable by cationic polymerization selected from the group consisting of

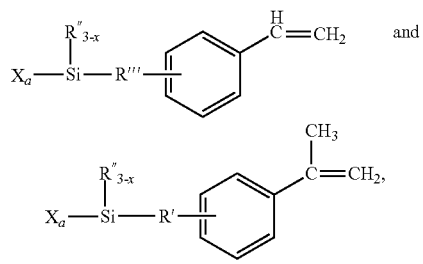

where (i) the R" groups are each independently selected from alkyl groups having 1 to 10 carbon atoms, aryl groups having 6 to 10 carbon atoms, and alkyl-aryl groups having from 7 to 12 carbon atoms; (ii) the R' and R''' groups are each divalent non-aromatic hydrocarbon groups having 0 to 6 carbon atoms; (iii) the X groups are halogen atoms; and (iv) n is 1, 2 or 3; and
  (b) one or more second monomers polymerizable by cationic polymerization which do not comprise a halosilyl group selected from aliphatic olefin monomers and diene monomers that provide said pendant alkyl groups; and
  wherein the therapeutic agent (A) comprises hydroxyl groups, amine groups, or both, and (B) is reacted with the halosilyl groups of said polymer portion to form said linkages.

14. A medical device comprising a therapeutic polymer comprising a polymeric portion and a covalently attached therapeutic agent which is linked to the polymeric portion via one or more linkages that hydrolyze in an aqueous environment,
  wherein said polymeric portion comprises a combination of unsubstituted pendant aromatic groups and substituted pendant aromatic groups,
  wherein said one or more linkages comprise an Si—N linkage, an Si—O linkage, or a combination of the same,
  wherein the polymer portion is formed from monomers comprising (a) a first halosilyl-group-containing monomer polymerizable by cationic polymerization selected from the group consisting of

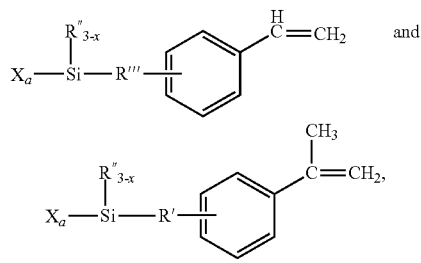

where (i) the R" groups are each independently selected from alkyl groups having 1 to 10 carbon atoms, aryl groups having 6 to 10 carbon atoms, and alkyl-aryl groups having from 7 to 12 carbon atoms; (ii) the R' and R' groups are each divalent non-aromatic hydrocarbon groups having 0 to 6 carbon atoms; (iii) the X groups are halogen atoms; and (iv) n is 1, 2 or 3 and (b) styrene and isobutylene,
  wherein the therapeutic agent (A) comprises hydroxyl groups, amine groups, or both, and (B) is reacted with the halosilyl groups of said polymer portion to form said linkages.

15. A therapeutic article comprising a therapeutic polymer comprising a polymeric portion and a covalently attached therapeutic agent which is linked to the polymeric portion via one or more linkages that hydrolyze in an aqueous environment, wherein:
  (a) said one or more linkages comprise an Si—N linkage, an Si—O linkage or a combination of the foregoing;
  (b) the therapeutic polymer has a linear architecture;
  (c) the therapeutic polymer comprises styrene monomers;
  (d) the polymeric portion comprises a saturated or unsaturated carbon backbone and a combination of alkyl groups directly pendant from said carbon backbone, unsubstituted aromatic groups pendant from said carbon backbone and substituted aromatic groups pendant from said carbon backbone and, optionally, a supplemental polymer; and
  (e) said therapeutic article is a medical device that is adapted for implantation or insertion into a lumen of the cardiovascular system.

16. The therapeutic article of claim 15 wherein the therapeutic polymer comprises both low $T_g$ and high $T_g$ monomers, wherein the low $T_g$ monomers are monomers that, when self-polymerized, form homopolymers displaying a $T_g$ that is below 20° C. and the high $T_g$ monomers are monomers that, when self-polymerized, form homopolymers displaying a $T_g$ that is above 50° C.

17. The therapeutic article of claim 15 wherein the covalently attached therapeutic agent is derived from an agent selected from anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

18. The therapeutic article of claim 15 comprising a polymeric release region that comprises said therapeutic polymer and said supplemental polymer.

19. The therapeutic article of claim 15, wherein said medical device is a coronary vascular or peripheral vascular stent.

20. A therapeutic article comprising a therapeutic polymer comprising a polymeric portion and a covalently attached therapeutic agent which is linked to the polymeric portion via one or more linkages that hydrolyze in an aqueous environment, wherein said polymeric portion comprises a saturated or unsaturated carbon backbone and alkyl groups directly pendant from said carbon backbone, wherein said one or more linkages comprise an Si—N linkage, an Si—O linkage, or a combination of the same, wherein said therapeutic article is a medical device that is adapted for implantation or insertion into a lumen of the cardiovascular system, wherein said medical device comprises a polymeric release region that comprises said therapeutic polymer and a supplemental polymer, and wherein the polymer portion is formed from monomers comprising:

(a) a first monomer polymerizable by cationic polymerization that comprises one or more chlorosilyl-group-containing monomers selected from:

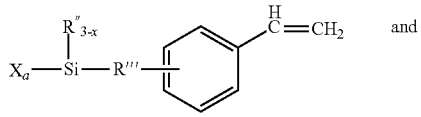 and

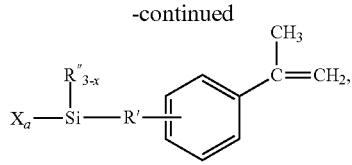

where (i) the R" groups are each independently selected from alkyl groups having 1 to 10 carbon atoms, aryl groups having 6 to 10 carbon atoms, and alkyl-aryl groups having from 7 to 12 carbon atoms; (ii) the R' and R''' are each divalent non-aromatic hydrocarbon groups having 0 to 6 carbon atoms; (iii) the X groups are halogen atoms;

and (iv) n is 1, 2 or 3; and (b) a second monomer polymerizable by cationic polymerization which does not comprise a silylchloride group and which is selected from:

(i) aliphatic olefinic monomers selected from propylene, 1-butene, isobutylene, 2-methyl-1-butene, 3-methyl-1-butene, pentene, hexene, cyclohexene, 4-methyl-1-pentene, vinylcyclohexene, octene and norbornene; and (ii) diene monomers selected from butadiene, isoprene, cyclopentadiene, cyclohexadiene, dicyclopentadiene, divinylbenzene, and ethylidenenorbornene;

and wherein the therapeutic agent:

(A) comprises hydroxyl groups, amine groups, or both, and is reacted with the silylchloride groups of said polymer portion to form said linkages; and (B) is derived from an agent selected from anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

* * * * *

UNITED STATES PATENT AND TRADEMARK OFFICE
CERTIFICATE OF CORRECTION

PATENT NO.        : 8,367,096 B2
APPLICATION NO.   : 11/184223
DATED             : February 5, 2013
INVENTOR(S)       : Robert E. Richard and Rudolf Faust Page 1 of 1

It is certified that error appears in the above-identified patent and that said Letters Patent is hereby corrected as shown below:

Specification, col. 3, line 62, after "groups" change, (e.g., C– –H), to --(e.g., C–O–H)--

Specification, col. 14, line 46, after "vectors" change, (e.g., PCOR), to --(e.g., pCOR)--

Claims, Claim 14, col. 18, line 31, after "(ii)" change, the R' and R', to --the R' and R'''--

Signed and Sealed this
Seventh Day of May, 2013

Teresa Stanek Rea
*Acting Director of the United States Patent and Trademark Office*